US008494875B2

(12) United States Patent
Broselow

(10) Patent No.: US 8,494,875 B2
(45) Date of Patent: Jul. 23, 2013

(54) SYSTEM AND METHOD FOR DETERMINING MEDICAL TREATMENT VALUES IN CHILDREN WITHOUT DATA ENTRY

(75) Inventor: James Broselow, Hickory, NC (US)

(73) Assignee: Ebroselow, Blacksburg, VA (US)

( * ) Notice: Subject to any disclaimer, the term of this patent is extended or adjusted under 35 U.S.C. 154(b) by 0 days.

(21) Appl. No.: 13/175,668

(22) Filed: Jul. 1, 2011

(65) Prior Publication Data

US 2011/0264462 A1      Oct. 27, 2011

Related U.S. Application Data

(63) Continuation-in-part of application No. 12/203,218, filed on Sep. 3, 2008, now abandoned.

(51) Int. Cl.
*G06Q 10/00*        (2012.01)

(52) U.S. Cl.
USPC ...... 705/2; 705/3; 702/19; 434/276; 128/898; 604/416

(58) Field of Classification Search
USPC ... 705/3; 434/276; 604/416; 702/19; 128/898
See application file for complete search history.

(56) References Cited

U.S. PATENT DOCUMENTS

| 4,926,885 | A  | * | 5/1990  | Hinkle          | 128/898 |
| 5,915,971 | A  | * | 6/1999  | Ramsay et al.   | 434/276 |
| 6,508,801 | B1 | * | 1/2003  | Fineberg        | 604/416 |
| 6,804,656 | B1 | * | 10/2004 | Rosenfeld et al.| 705/3   |
| 2002/0169636 | A1 | * | 11/2002 | Eggers et al. | 705/3 |
| 2005/0216203 | A1 | * | 9/2005  | Vaidya et al. | 702/19 |

OTHER PUBLICATIONS

Google patents search, Mar. 22, 2013.*
Google European patents search, Mar. 22, 2013.*

* cited by examiner

*Primary Examiner* — Dilek B Cobanoglu
(74) *Attorney, Agent, or Firm* — Shumaker, Loop & Kendrick, LLP

(57) ABSTRACT

A system is provided for providing patient treatment values in real-time, including: a database module comprising a database having a plurality of predetermined categories of patient selection criteria, patient condition categories, treatment types and precalculated treatment doses based on the predetermined categories and patient selection criteria; an input module in communication with the database module for inputting one or more of patient selection criteria, patient condition categories and treatment type at time of patient treatment; and a display module in communication with the database module and the input module for displaying a precalculated treatment dose based on one or more inputted patient selection criteria, patient condition categories and treatment type at time of patient treatment.

13 Claims, 15 Drawing Sheets

| 3kg | 4kg | 5kg | 6-7kg | 8-9kg | 10-11kg | 12-14kg | 15-18kg | 19-233kg | 24-29kg | 30-36kg |

QuickDose
15-18 kg

- RESUSCITATION
INFUSIONS
ANAPHYLAXIS
RSI
SEIZURES
RESPIRATORY MEDS
FLUID & BLOOD THERAPY
REHYDRATION THERAPY
ELECTROLYTE ABNORMAL
DKA
BURNS
TOXICOLOGY
GASTROINTESTINAL AGENTS
STEROIDS
INTERCRANIAL PRESSURE
CHEMICAL WEAPONS
PRESCRIBING GUIDE
(QUICK REFERENCE) ▷
(ANTIBIOTICS) ▷
(PAIN & SEDATION) ▷
- NEWBORN RESUSCITATION
DOSING KEY
TRADE/GENERIC INDEX

| ADENOSINE 1st DOSE IV | 0.1 mg/kg DOSE | | | | | (ADENOCARD) |
|---|---|---|---|---|---|---|
| | | | | | 15-18kg | |
| | | | | | 1.7 mg | |
| 3 mg/mL | | | | | 0.57 mL | |

114 ⟵ 112

PUSH DIRECTIONS
IVP RAPIDLY OVER 1-2 SECONDS, FOLLOW WITH A RAPID BOLUS 5-10 mL NORMAL SALINE (NS) IVP. FOLLOW WITH SECOND DOSE OF 0.2 mg/kg IF UNSUCCESSFUL.

REMARKS
NOTE: TRY TO PLACE PATIENT'S IV ACCESS CLOSE TO THE HEART (e.g. ANTECUBITAL) SINCE PLACEMENT IN OTHER VEINS MAY RESULT IN TREATMENT FAILURE.
BRONCHOSPASM AND RESPIRATORY FAILURE MAY OCCUR IN ASTHMATIC PATIENTS, WATCH FOR RESPIRATORY DISTRESS.

FIG. 6

| 3kg | 4kg | 5kg | 6-7kg | 8-9kg | 10-11kg | 12-14kg | 15-18kg | 19-233kg | 24-29kg | 30-36kg |

PRESCRIBING GUIDE

- RESUSCITATION
- INFUSIONS
- ANAPHYLAXIS
- RSI
- SEIZURES
- RESPIRATORY MEDS
- FLUID & BLOOD THERAPY
- REHYDRATION THERAPY
- ELECTROLYTE ABNORMAL
- DKA
- BURNS
- TOXICOLOGY
- GASTROINTESTINAL AGENTS
- STEROIDS
- INTERCRANIAL PRESSURE
- CHEMICAL WEAPONS
- PRESCRIBING GUIDE
- (QUICK REFERENCE) ▷
- (ANTIBIOTICS) ▷
- (PAIN & SEDATION) ▷
- ●NEWBORN RESUSCITATION
- DOSING KEY
- TRADE/GENERIC INDEX

PLEASE SELECT A WEIGHT OR COLOR TAB ABOVE TO CONTINUE

| ALLERGY 15-18 kg | ANTIBIOTICS 15-18 kg | ANTIFUNGALS 15-18 kg |
| ANTI INFLAMATORY 15-18 kg | ANTIPARASITIC 15-18 kg | ANTIVIRAL 15-18 kg |
| CROUP 15-18 kg | FEVER/PAIN 15-18 kg | GASTROINTESTINAL 15-18 kg |
| REACTIVE AIRWAY 15-18 kg | | |

SYSTEM AND METHOD FOR DETERMINING MEDICAL TREATMENT VALUES IN CHILDREN WITHOUT DATA ENTRY

CROSS-REFERENCE TO RELATED APPLICATION

This application is a continuation-in-part of U.S. patent application Ser. No. 12/203,218 filed Sep. 3, 2008 now abandoned and entitled Method for Determining Medical Treatment Values Without Data Entry, which is incorporated by reference in its entirety for all purposes.

BACKGROUND

Acute emergencies in Children are relatively rare. However, when they do occur, they are usually treated in a general practice setting rather than in a specialized children's practice or hospital, and the child's care is usually administered by paramedics, physicians, nurses and pharmacists, most of whom have little experience with the complex demands of ordering, preparing or administering drugs acutely to children. Adults' medications are standardized and frequently come in "amps" that allow immediate accurate dosing, administering pediatric drugs require multiple layers of complex, error prone calculations where misplacing a decimal point can lead to fatal, 10-fold errors (so-called "death by decimal point"). Despite the relative infrequency of acute emergencies in children, adverse drug events happen to children three times as often as to adults. Simulated studies demonstrate that when under pressure, nurses can commit errors 25% of the time when making IV drug calculations for children and errors are often only caught 20% of the time. Even the most sophisticated emergency care providers can feel uncomfortable when treating life-threatening emergencies in children. They know what to do, but they are afraid of making mistakes because of size and age-related variables. As a result, emergency healthcare providers are forced not to act or to delay needed treatment in order to check and recheck appropriate treatments so as to avoid doing harm. Hospitals have a critical need to reduce errors and treatment time in emergency pediatric care. Dosing calculations for children are notoriously error-prone.

The very process of medication administration to children under even normal circumstances is complex. First, the dose itself must be calculated based on the weight of the child, which can vary from 500 gms for neonatal infants to several hundred kilograms for older children. Each drug dose is calculated by formulas, typically expressed in mgs/kg/dose per day. Once the dose is calculated in mgs, it must be delivered in mLs of various concentrations which represent the ordered dose. In addition and further complicating the issue, a given drug may have multiple doses for different treatments. For example, Diazepam is a drug that is given to stop seizure activity in a dose of 0.2 mg/kg, but is also given to sedate a child in a different dose of 0.1 mg/kg. Once the dose is ordered for the correct treatment, a nurse would look at the concentration of the drug in the vial and set up a ratio to determine the correct volume that represents the dose ordered.

Once that volume is determined the nurse needs to know, or lookup, whether the drug needs additional dilution prior to administration. For instance, a drug such as amiodarone given for acute cardiac arrhythmias can lead to a dangerous blockage if not sufficiently diluted or if pushed too fast through the line. Other drugs can be administered without dilution, but the rate of administration varies from drug to drug. Also, the amount of fluid used to further dilute the drug can vary with the size of the child as well.

Nurses that treat adults tend to know this information because the doses tend to be standardized and acute emergencies are treated in adults on a regular basis. This is not the case with pediatric emergencies outside of pediatric ICUs and some very busy pediatric emergency departments. Even there, rare emergencies requiring special treatments such as very high potassium level in a child with renal failure and in cardiac arrest, or administering a complicated infusion such as an alprostadil to a neonate with a critical heart lesion, are still rare occurrences. Not only must these drugs be given error free, but time is of the essence. Finally, it is important that the steps leading to the correct preparation and administration of a drug are transparent to all members of the team so that errors can be recognized immediately and corrected.

A particular concern is the correct administration of continuous infusions to children. These drugs are ordered in micrograms per kilograms per minute. Until recently, a single formula utilizing a child's weight was utilized to calculate how to prepare the infusion. Recent regulations now prohibit the use of this formula in hospitals so that standard concentrations need to be utilized. Also, it is not enough to merely set the infusion at a rate that provides the proper dose, but it is also critical that the dose given is not so small that an infusion pump cannot be used to administer the dose, or too large a volume for the size of the child. Because of these issues, complex software systems have been designed to determine the concentrations to be carried in the pharmacy for a large number of standardized infusions. The standard concentrations are stored in the pharmacy so that they are already prepared beforehand. Unfortunately, certain drugs cannot be mixed in advanced. For instance, a rarely administered infusion of nor-epinephrine may be need at the bedside of a child in shock and must be mixed and delivered immediately and in real time. A pharmacist receiving an order for this drug, (if there is a pharmacist there) would be expected to be familiar with the preparation administration information for adults, but may have never mixed the particular drug for a child. Although a software system may be available in one of their pharmacy programs, it may still take a pharmacist additional time to locate and verify the proper administration. Then, even if this computer program is a simple one, the pharmacist would still need to determine exactly how to enter the information to calculate how to mix the drug. It would not be unusual for this process to take an hour in a community hospital, especially at night when there may be less help available. Once the drip has been mixed, it must be delivered to the bedside. At this point, it may not be clear to those at the bedside that it was mixed correctly and the medication is typically just administered without knowing how it was mixed or whether the calculations are correct. This is exacerbated by the fact that transport teams from children's hospitals almost always throw away the infusions that are mixed at a community hospital and remix them themselves prior to transfer.

There have been many attempts to impact these issues with various types of technologies and software solutions. Many physicians carry PDAs or smart phones that access the proper doses of medications for various indications. Even these systems require that the formula then be calculated to get the exact dose. Even if there is a calculator function in the program, it usually requires data entry to set the weight and also the drug itself needs to be found. Once this process is done, the physician can call out the dose to be given. However it is not clear to the nurse administering the dose that it was ordered correctly. A recent study determined that a nurse is not likely to recognize 80% of ten-fold errors for drugs that are not commonly given to children. Even if the dose is correct, the nurse would then need to calculate the volume in milliliters that represented that dose. In practice, this calculation is often done by hand, on the bed sheet, or on a paper towel. Once the calculation is complete, it is still not always clear to another nurse checking the dose that it was done correctly. It is also common for nurses not to know exactly how rapidly a dose must be given, whether the dose needs further dilution, and if so, exactly how much diluents are needed, all of which also change with the size of the child. To answer these questions, nursing references should be checked prior to administration, but these resources are typically not available at the bedside and if accessed, tends to be encyclopedia in scope. It takes time to find the correct medication, and takes additional time to look up in a book or scroll down in a software system to find the relevant facts. All of these safeguards take additional time and are typically not done when time is of the essence.

There is clearly a need to simplify and standardize this process to improve care and reduce medical errors for acute medication administration in children. Data entry should be minimized or eliminated entirely because it is error prone, takes time and is not transparent to others in the team. Also, even the simplest software system takes time to get oriented on how to enter data correctly. This again, takes critical time and can be quite challenging when dealing with a life threatening emergency in a child.

SUMMARY

Therefore, it is an object of the invention to provide a system that permits the determination of medical treatment values without data entry.

It is another object of the invention to provide a system that permits the determination of medical treatment values at bedside, and in a manner that can be verified by others involved in medical care of the patient.

It is another object of the invention to provide a system that permits the determination of medical treatment values that includes administration instructions and techniques provided with the medical treatment value.

It is another object of the invention to provide a system that permits the determination of medical treatment values with a language that describes the clinical indication relating to each dose.

It is another object of the invention to provide a system that permits the determination of medical treatment values where multiple sources of information are distilled into a preferred source for the administration of a particular drug in a given clinical circumstance.

It is another object of the invention to provide a system that permits the determination of medical treatment values where all of that information is presented in a standard format allowing rapid orientation to content.

It is another object of the invention to provide a system that permits the determination of medical treatment values where standard formats are stored as a graphic unit and accessed as a whole with only one or two keystrokes to allow rapid access.

It is another object of the invention to provide a system that permits the determination of medical treatment values where all data is pre-determined and easily verified by all members of a clinical team.

It is another object of the invention to provide a system that permits the determination of medical treatment values to be displayed at the bedside or the operating room with access preferably by touch screen and a large computer display.

It is another object of the invention to provide a system that permits the determination of medical treatment values with a system that is uploaded with text indicia rather than calculated indicia.

These and other aspects of the invention are provided in a method of providing patient treatment values for predetermined medical treatments without the need for treatment value calculations at the time of treatment, includes the steps of providing a database provided with predetermined categories of patient selection criteria and patient condition categories, and determining treatment values for patients based on the selection criteria. The data is entered into a database programmed to receive the treatment values correlated to the selection criteria at a time in advance of patient treatment. To treat a patient, the patient selection criteria is determined and selected, a patient condition is determined and selected, and the database returns a treatment value correlated to the patient selection criteria.

According to one embodiment of the invention, the predetermined categories of patent selection criteria are patient body weight ranges.

According to another embodiment of the invention, the predetermined categories of patent selection criteria are a range of selectable different colors.

According to another embodiment of the invention, the predetermined categories of patent selection criteria are arranged in rows and the patient condition categories are arranged in columns.

According to another embodiment of the invention, the treatment values are selected from the group consisting of equipment sizes, drug dosages, drug dosage prescribing and sequencing values.

According to another embodiment of the invention, the method includes the step of programming the database to white out columns containing non-selected patient selection criteria.

According to another embodiment of the invention, the method includes the step of providing an entry screen that allows entry into a desired patent condition category with a single selection activity.

According to another embodiment of the invention, the predetermined categories of patent selection criteria are the predetermined patient condition categories selected from the group consisting of Resuscitation, Infusions, Anaphylaxis, RSI, Seizures, Respiratory Medicines, Fluid and Blood Therapy, Rehydration Therapy, Electrolyte Therapy, D.A., Burns and Toxicology.

BRIEF DESCRIPTION OF THE DRAWINGS

Some of the objects of the invention have been set forth above. Other objects and advantages of the invention will appear as the description of the invention proceeds when taken in conjunction with the following drawings, in which:

FIG. 6 is a representation of a chart showing the selected treatment doses for a selected medication and weight range according to an embodiment;

FIG. 10 is a representation of a prescribing guide according to an embodiment;

FIG. 11 is a representation of an antibiotics guide according to an embodiment;

Figure 13:
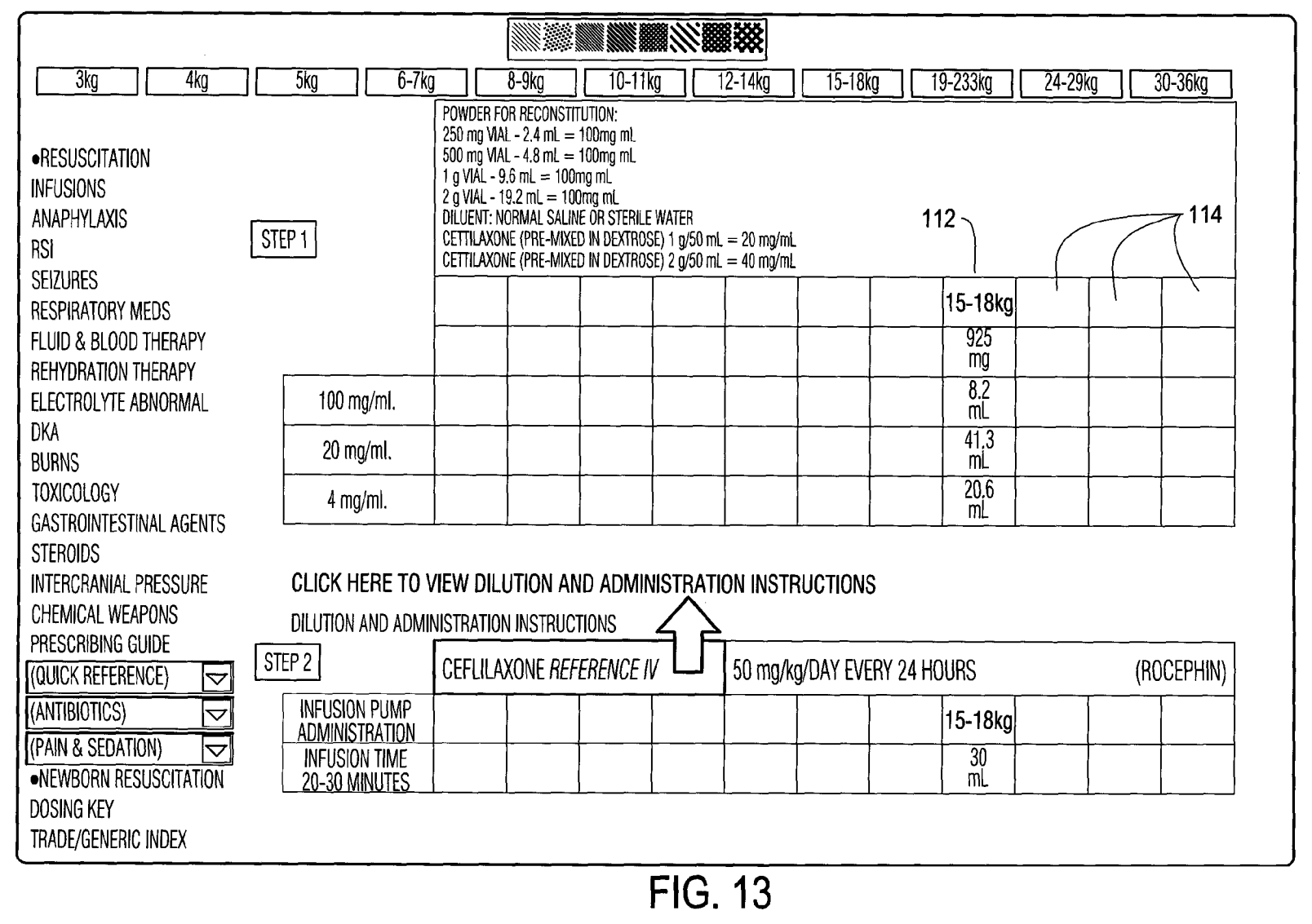

FIG. 13 is representation of a listing of dosages common antibiotics for a given weight range according to an embodiment;

DETAILED DESCRIPTION OF EMBODIMENTS

Embodiments describes herein set out a process for solving the problems of the prior art. First, the pharmacology of each acute drug is reviewed in advance as it relates to acute administration in children. Next, an interface is developed that allows all relevant information to be conveyed on a single screen. Third, a "dosing grid," is accessed with an exact grid for a particular child size by determining a code, for example scanning an NDC barcode, from the drug. Scanning the drug helps to prevent transcription, reading and other human errors that can contribute to administering a dangerous or even fatal dose. A child's weight may also be entered, for example scanned from a barcode on the armband or patient chart. If no weight barcode is present, putting the weights in zones would allow a single click or touched access that corrects grid. The zones, may be represented by colors for example. For all drugs with a single indication, these two scans would access the exact dose, conversion in milliliters, preparation and administration information, and other information. For a drug with multiple indications or treatments, scanning would then access as a screen that asks first to identify the correct indication or treatment. For example, dexamethasone is a steroid that is used in different doses for cerebral edema, airway edema croup, anti-inflammatory, anaphylaxis, etc. The screen would list these indications or treatments and could be selected by a mouse or touch screen to access all of the relevant information. Even if these complex operations. In general, a single entry at most would be all that is required to determine or verify a correct dose. A dosing grid would include that same indication so that anyone looking at the grid could see the drug name, patient weight, conversion in milliliters, dilution and administration time for that particular drug for that exact indication. With minimal searching, complex infusion mixing instructions could be simplified by simply stating how much to draw out of the vial and put into a bag of fluid. These instructions would be direct and simple without needing additional data entry and to a standard infusion calculation program.

A major advantage of scanning the NDC code is to ensure that all conversions and dilutions are based on the actual concentration and the amp. A recent well publicized error occurred in newborn twins, for example, when a huge dose of heparin was administered by mistake because a nurse thought the concentration of the vial was the concentration that she usually used, but in fact she put the wrong in the drawer. Scanning the vial as above would have prevented this error. Also recently, a child died in a children's hospital due to a ten-fold error in calcium being given. Again, a system such as the embodiments described above would have avoided this error. Indeed, the term "death by decimal point" has described this particular hazard that children face when being given medications.

Figure 1:
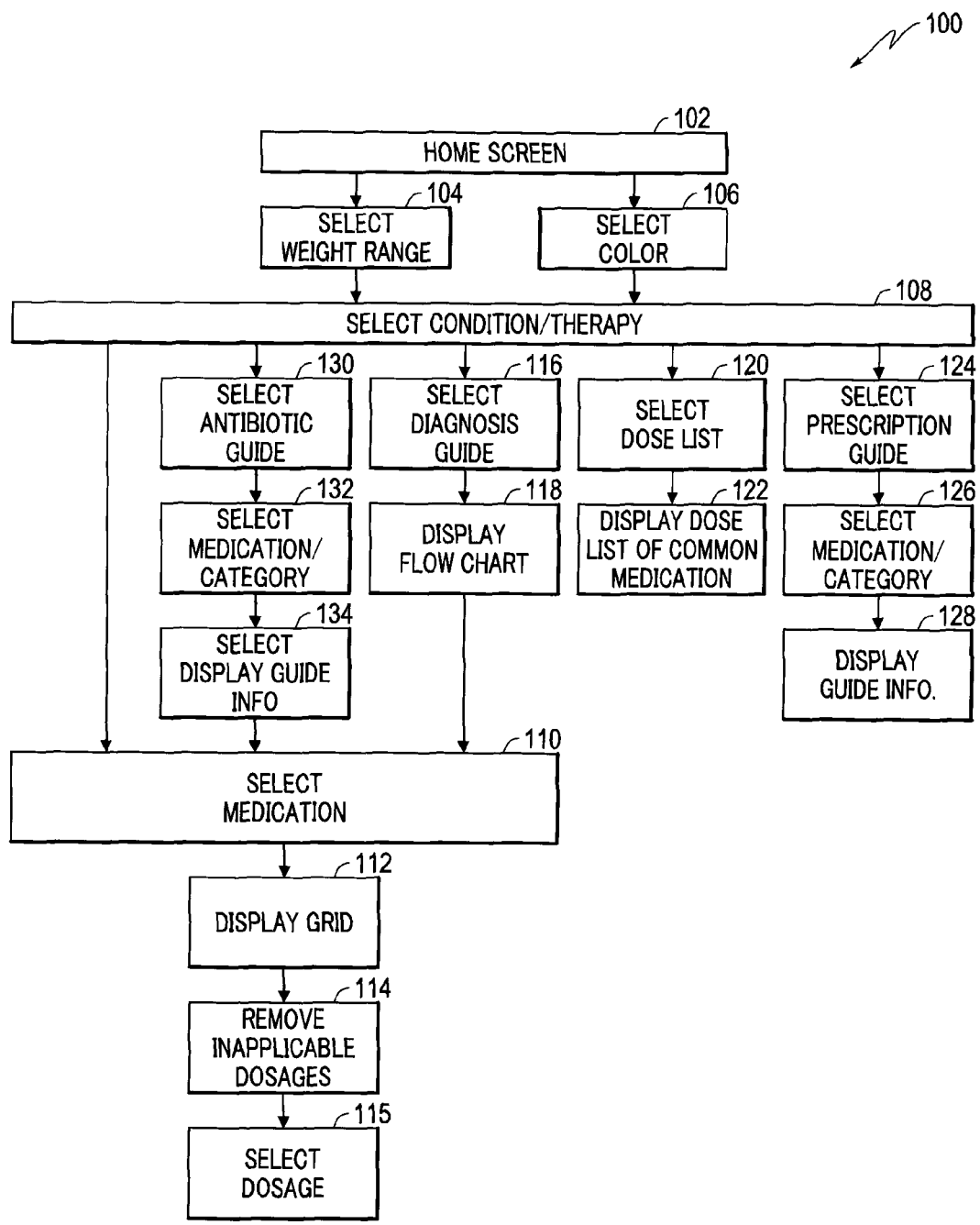
FIG. 1 is an illustration of a workflow method according to an embodiment.

Referring now specifically to the drawings, an entry screen is shown in FIG. 1 that permits the user to quickly determine a selected one of many values. The values are entered into the system as text during system development and maintenance. The system contains no values that are calculated by the system or that must be entered by the user during patient treatment. This prevents miscalculated values resulting from hasty, careless or mistaken data entry. The text values are entered, double-checked and verified in a controlled, non-patient, stress-free environment. The user is thus freed from the task of remembering and correctly entering values in an emergency situation.

The system is thus passive and user-friendly, highly graphical and operates in real time. Standardized formatting means that the user can quickly become familiar with the layout, thus further increasing speed and accuracy.

The application shown is a system and method particularly adapted for use in pediatric emergency situations commonly found in hospital emergency rooms and in EMS facilities or vehicles. Other applications of the system and method include general medical practice, geriatric care and veterinary care. A color-coding regime based on variables such as weight ranges may be used. Example embodiments are weight-based, but can be based on length correlated to lean body mass. In the application illustrated in FIG. 1, the user may start on the entry screen by picking a category, such as "resuscitation" based on the immediate observation by the user of the patient's condition and the needed intervention and "clicking" on the "Resuscitation" Category. The system may be further entered by knowing that the patient is a coded "purple", or may weigh or estimate the weight of the patient without regard to color coding. Clicking on the "Purple" box at the top of the chart immediately opens a table. Knowing the "color" of the patient, i.e., purple, yellow, etc., permits a wide range of treatment selections to be made without calculations, weight or age estimates.

Turning now to the drawings, FIG. 1 is an illustration of a workflow method according to an embodiment of the invention. Beginning with entry screen 102 either a weight range 104 or a color corresponding to that weight range 106 is selected. A condition or therapy is then selected at which point a number of options are available. The most common option would be to simply select the medication 110, at which point a grid is displayed for that particular weight range 112 and inapplicable doses are whited out or otherwise hidden 114. It is then a simple matter of selecting the dosage 115 at which point an administration flowchart 118 or prescription guide 128 for example can be displayed. Another option is to select a diagnosis or treatment guide 116 based on known symptoms, a flowchart showing next steps 118 can be displayed. If a medication is required, a link to the medication selection screen may be provided 110. Another option is to select a dose list for common medications 120 once the weight range is determined, a dose list of common medications for that weight range 122 may be displayed. That screen may link to a medication selection screen as well 110. Another option is to select a prescription guide 124 for a specific range of medications or categories. Once the medication or category is selected 126, guide information for that particular medication or category is displayed 128. Another option is to select an anthriotic guide 130 similar to selecting medication or dose list, a medication or category can be selected 132 and guide information for that particular antibiotic or family of antibiotics can be displayed 134. At this point, a specific antibiotic may be selected in the medication selection screen 110.

Figure 2:
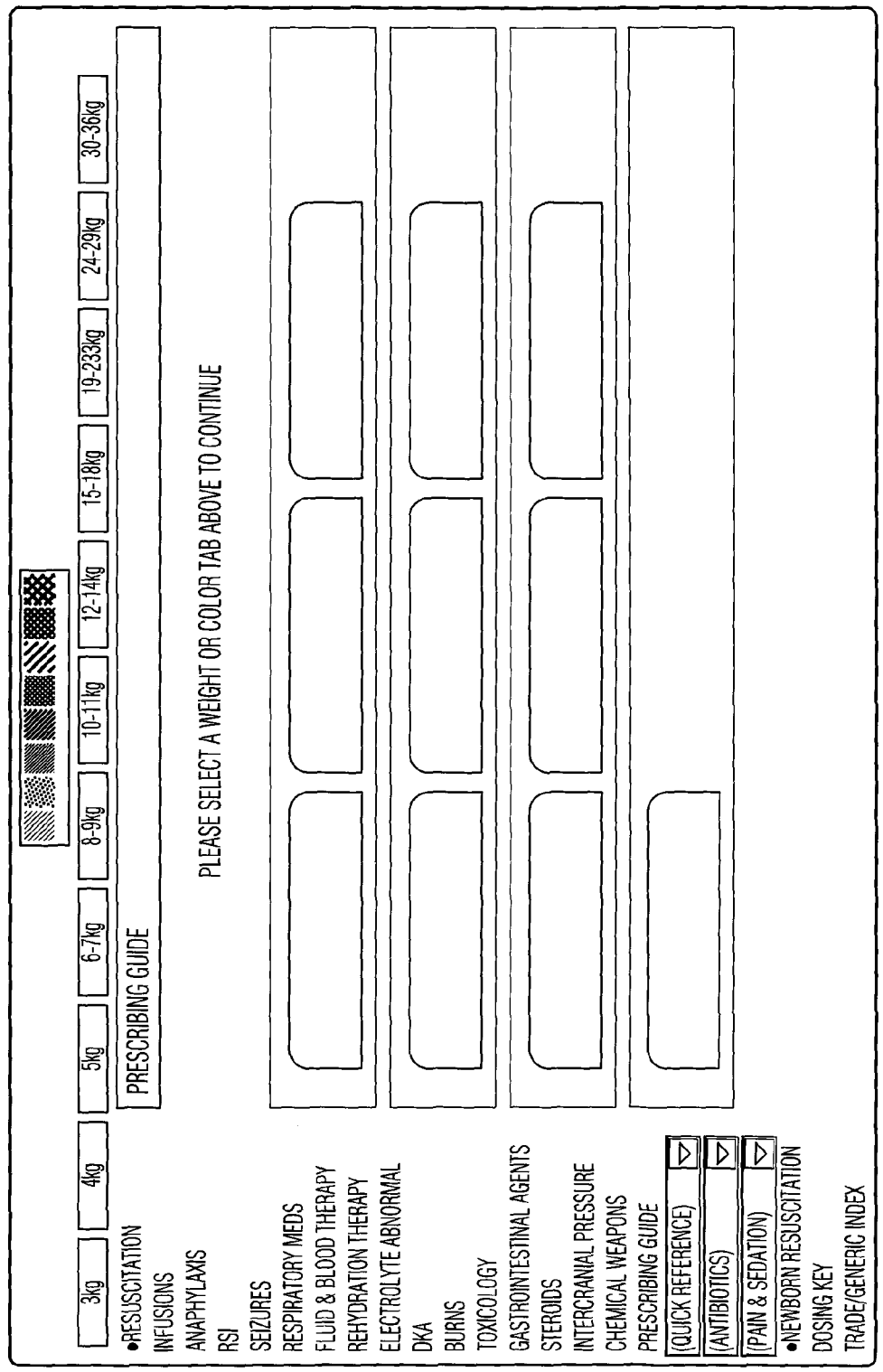
FIG. 2 is a representation of an entry screen according to an embodiment.
Figure 3A:
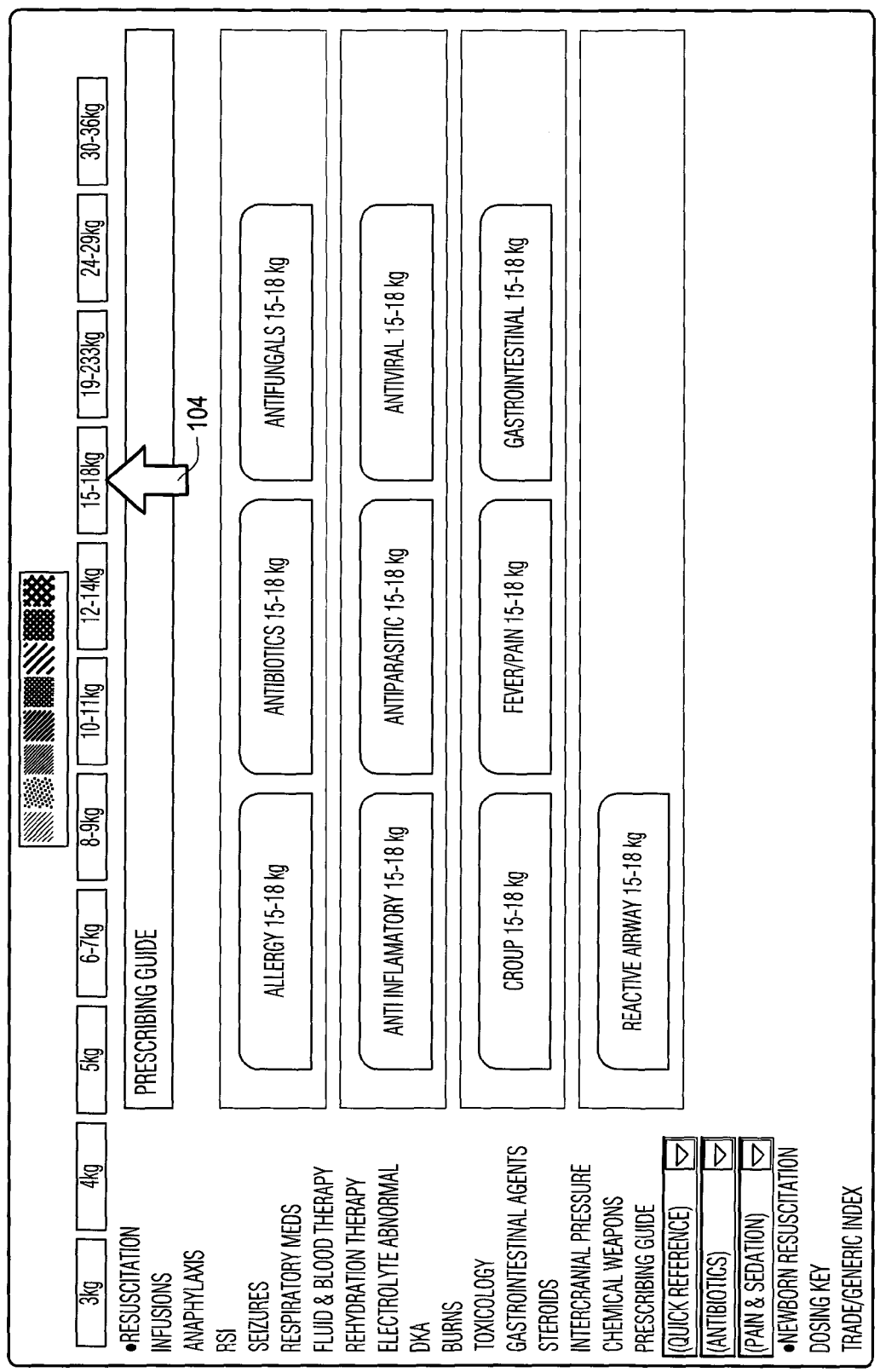
FIG. 3a is a representation of a weight selection step according to an embodiment.
Figure 3B:
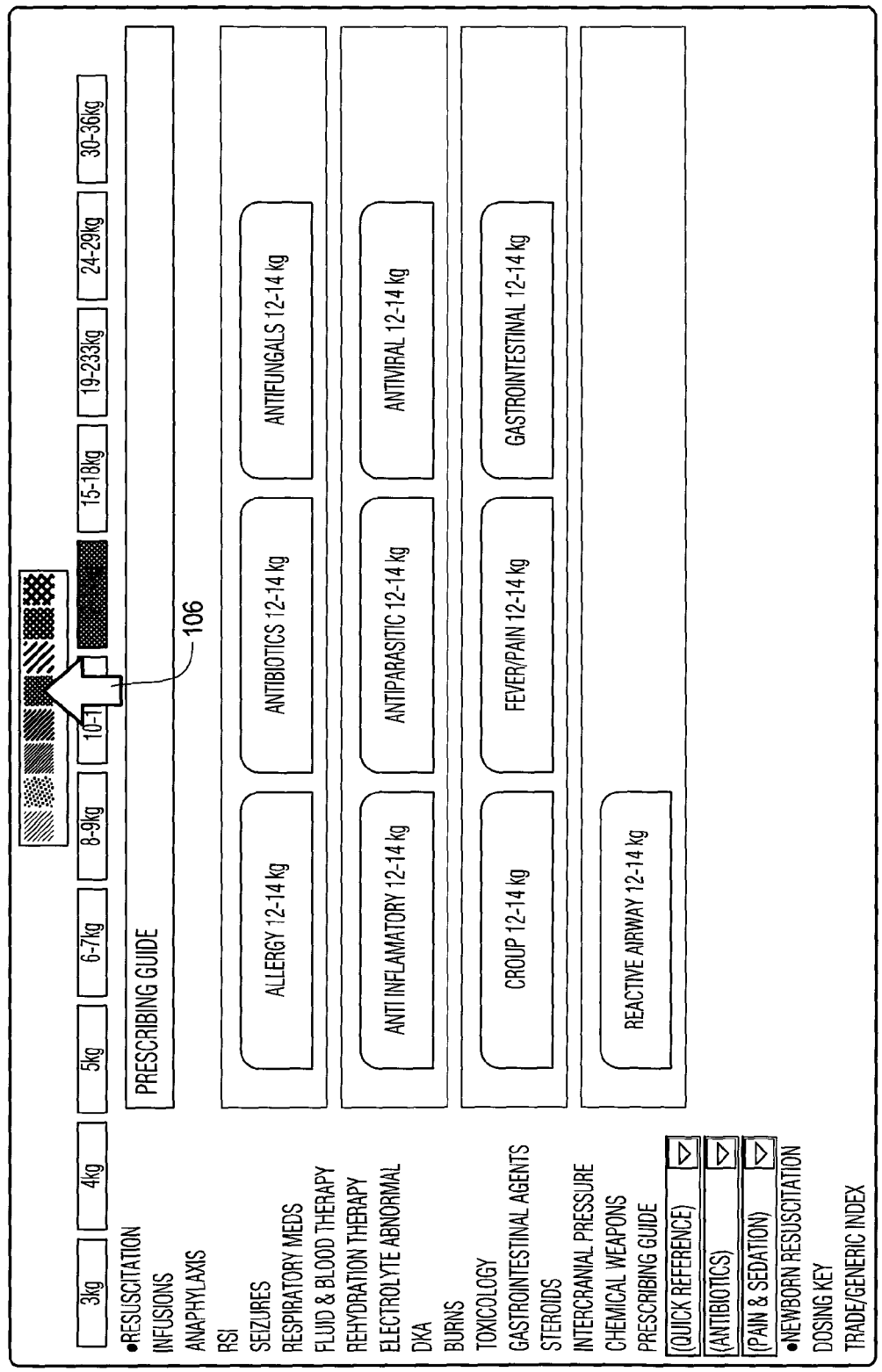
FIG. 3b is a representation of a color selection step according to an embodiment.
Figure 4:
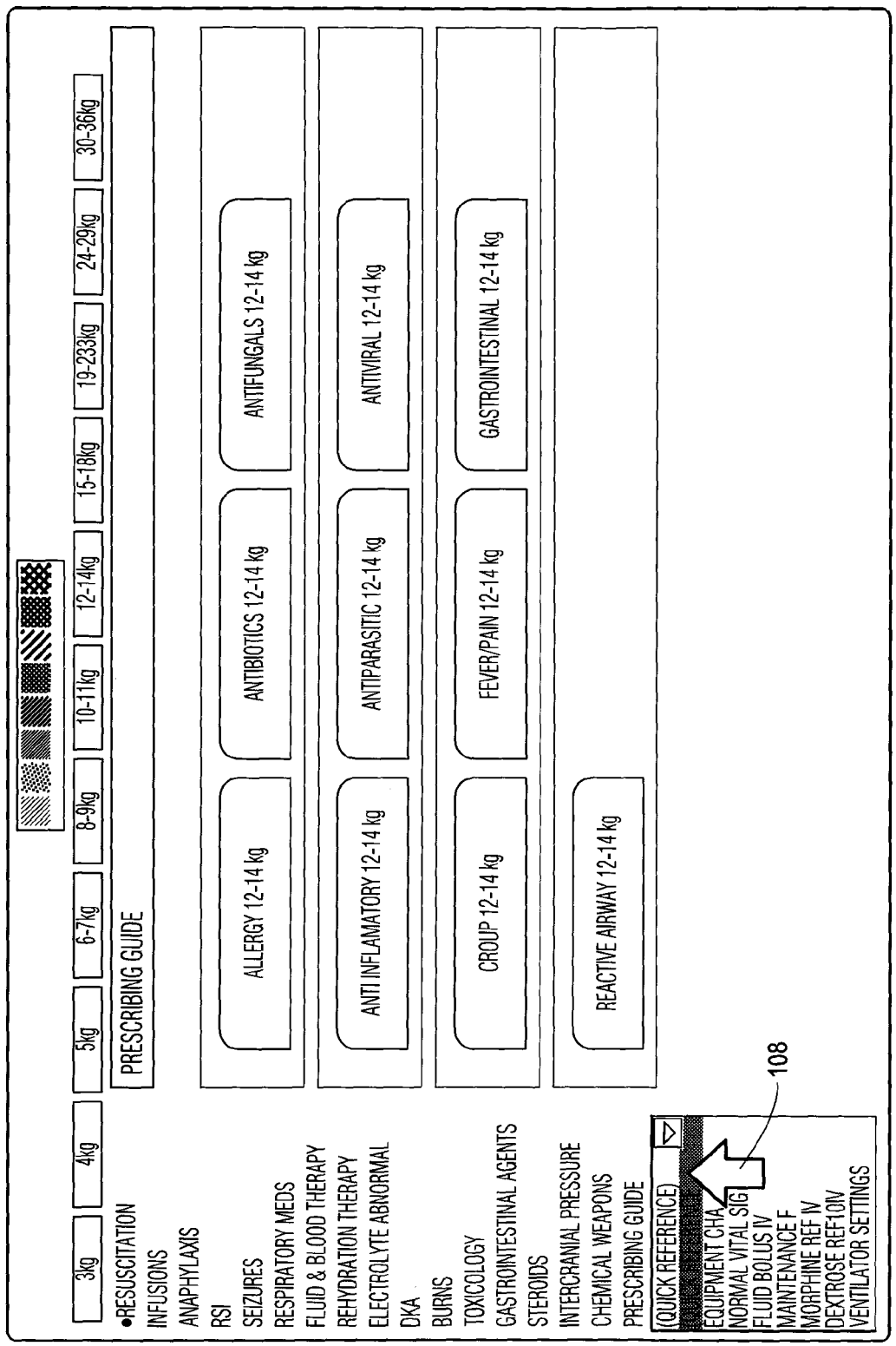
FIG. 4 is a representation of a treatment selection step according to an embodiment.
Figure 5:
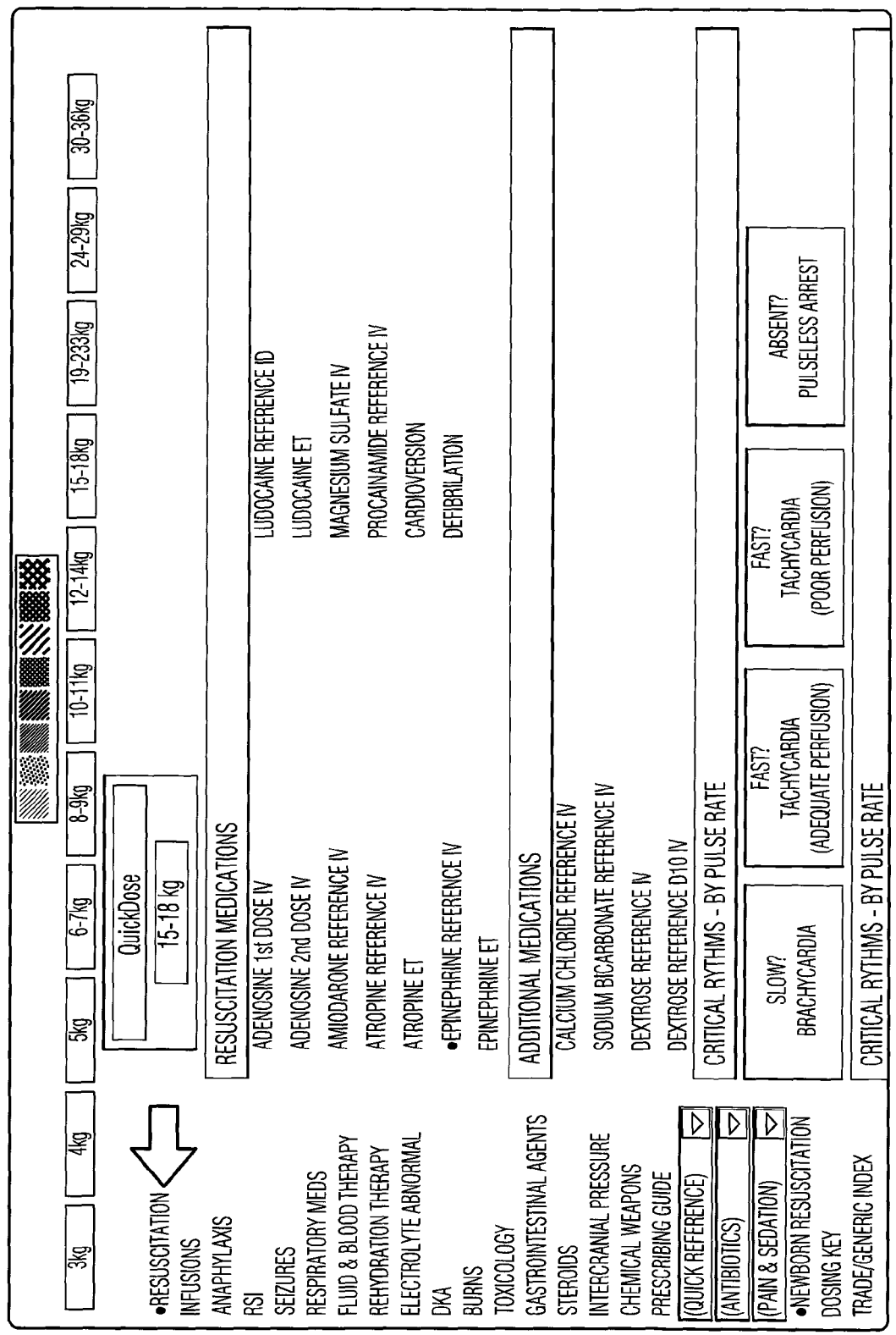
FIG. 5 is a representation of a medication selection step according to an embodiment.

FIG. 2 is a representation of an entry screen 102 according to the above embodiment. In a single interface, weight ranges, color codes, common conditions and treatments and other options are available in a single screen. FIGS. 3a and 3b illustrate the selection process for weight ranges 104 and color codes 106, respectively. Once the weight range is selected, additional options such as prescribing guides for children of that particular weight range of color code are provided. FIG. 4 shows additional options, for example through a drop-down menu. FIG. 5 discloses a selection of condition or therapy 108. In this figure, a list of common medications for each selection condition or therapy is presented. FIG. 6 shows a medication selection grid that includes the display of the correct dosage for a given drug and weight range 112 and also hides, whites out, or otherwise deemphasizes other inapplicable ranges 114 to prevent errors.

Figure 7:
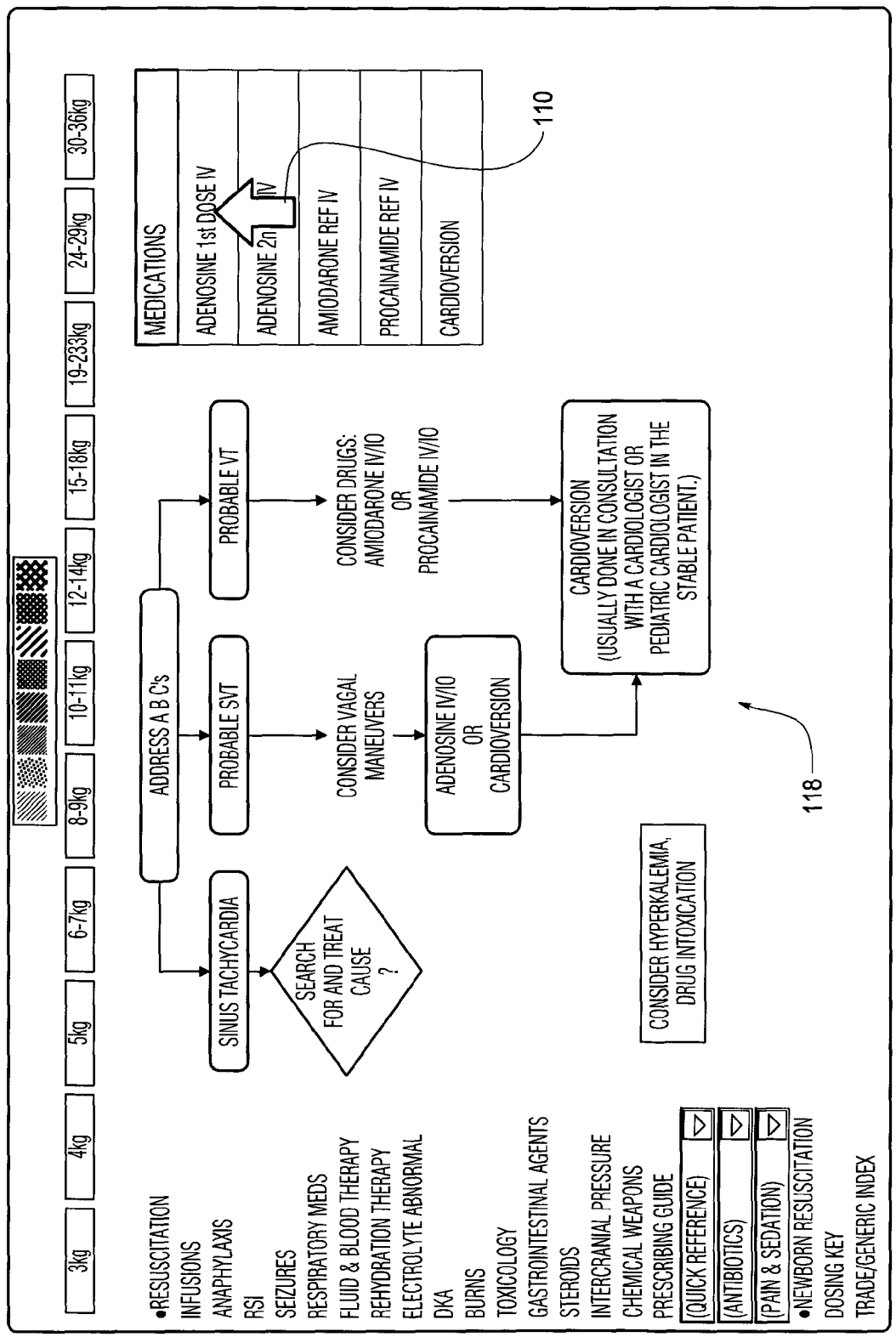
FIG. 7 is a representation of a diagnosis and treatment guide displaying a treatment flowchart according to an embodiment.
Figure 8:
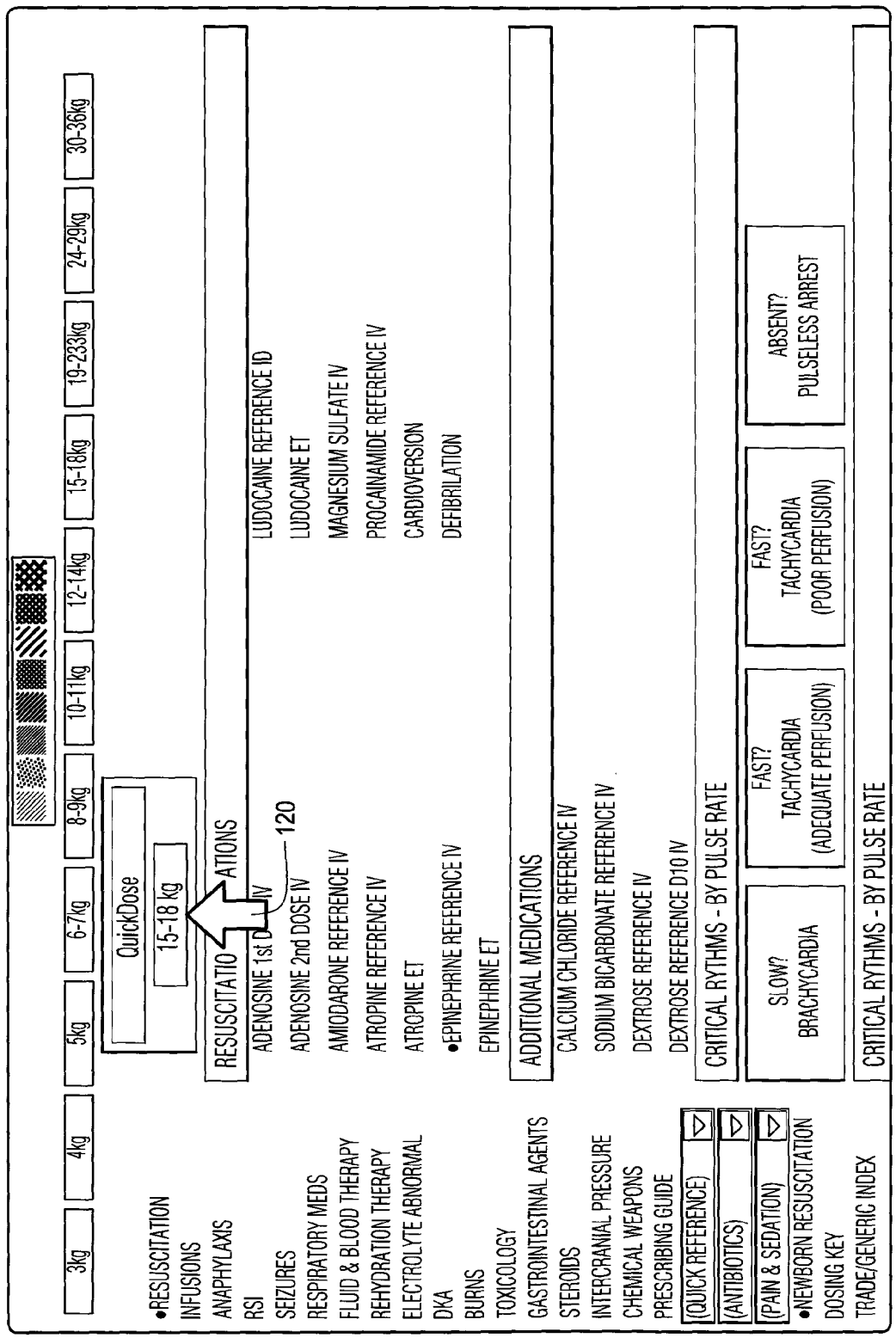
FIG. 8 is a representation of a listing of common medications for a given weight range according to an embodiment.
Figure 9:
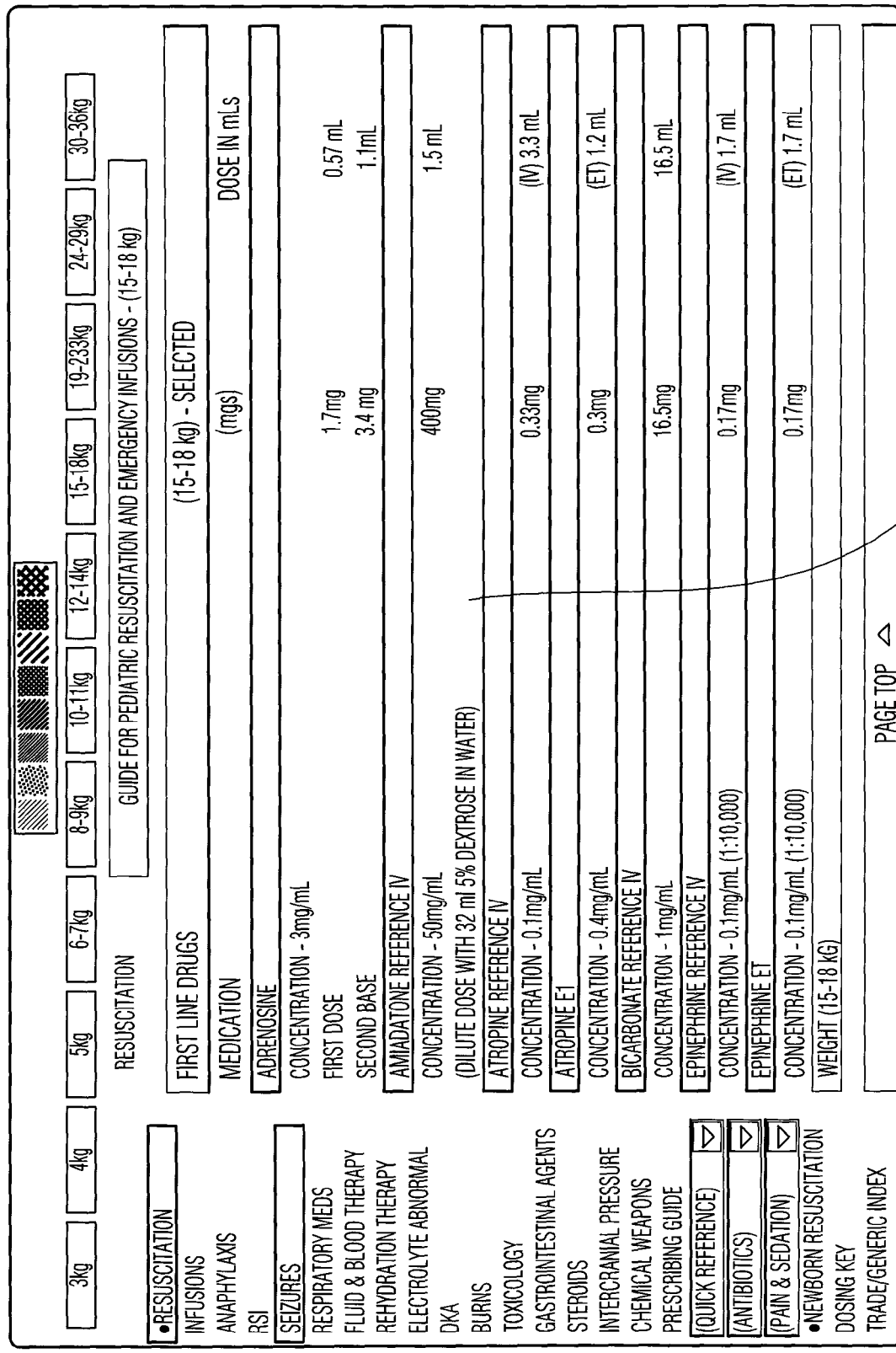
FIG. 9 is a representation of a listing of dosages common medications for a given weight range according to an embodiment.

FIG. 7 shows a flowchart for diagnosis and treatments of specific symptoms 118, as well as referenced medications which link to the medication selection 110. FIG. 8 shows a selection of the dose list for a 15-18 kg child 120. As shown in FIG. 9, selecting this option will list common medications for the child's weight range and symptoms or treatment 122.

Figure 11:
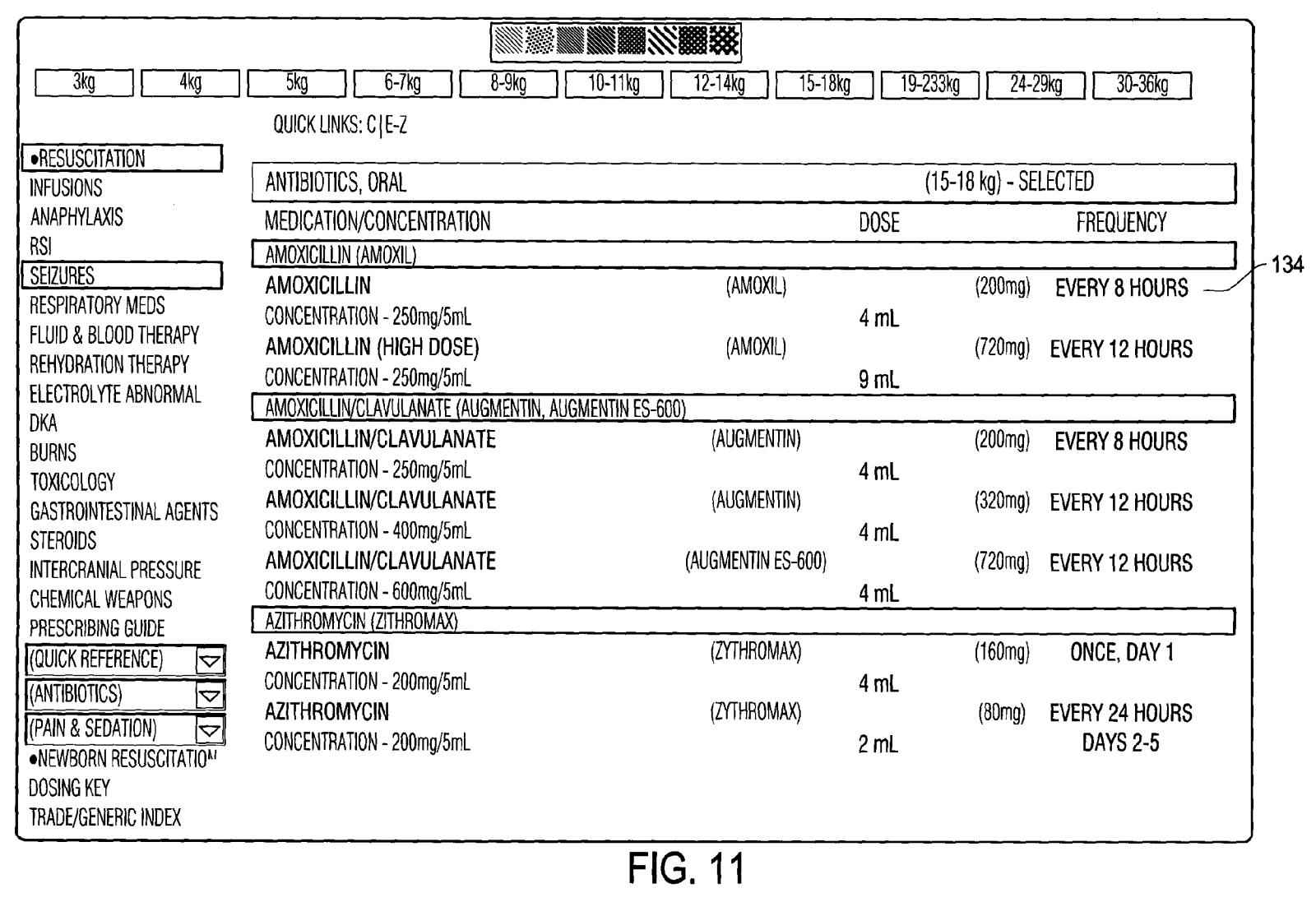
Figure 12:
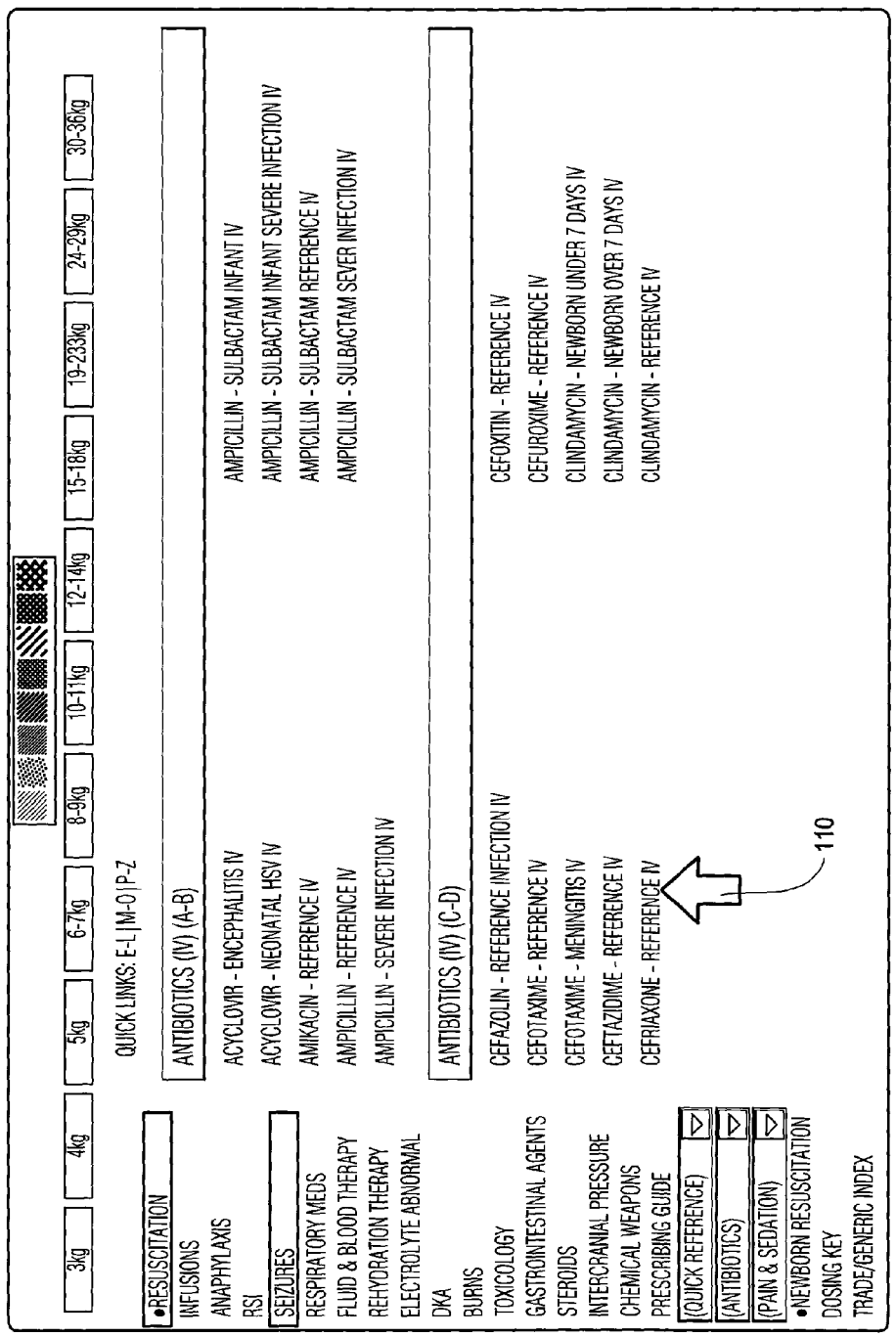
FIG. 12 is a representation of a listing of common antibiotics according to an embodiment.

FIG. 10 shows a prescribing guide for common medications for a given weight range 126. FIG. 11 discloses an antibiotic guide 134 for a given weight range along with prescription and dosage information. Finally, FIG. 12 discloses a listing of specific antibiotics for different weight ranges, child types, and conditions 132. Once the antibiotic is selected 110, the grid is displayed 112 for that particular weight range and drug, while hiding other inapplicable doses 114.

Figure 15:
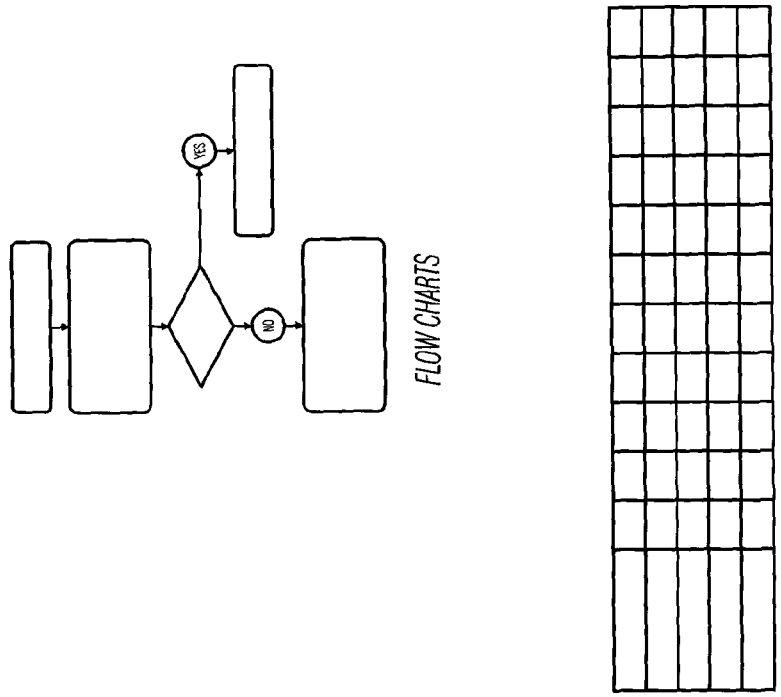
FIG. 15 is a representation of a diagnosis and treatment guide displaying a treatment flowchart according to an embodiment.
Figure 14:
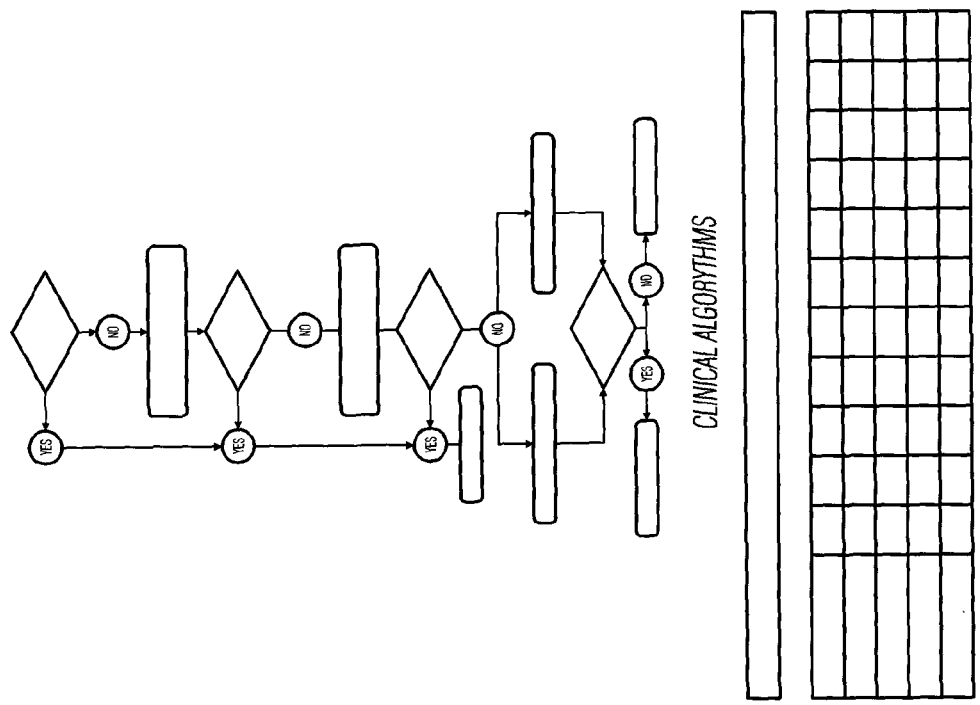
FIG. 14 is a representation of a diagnosis and treatment guide displaying a treatment flowchart according to an embodiment.

FIG. 14 shows a representation of a diagnosis and treatment guide displaying a treatment flowchart according to an embodiment, such as a clinical algorithm for diagnosis and/or treatment of, for example, respiratory depression/desaturation. FIG. 15 shows a representation of a diagnosis and treatment guide displaying a treatment flowchart according to an embodiment, such as a flowchart 118 for the administration of midazolam followed by ketamine.

Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

What is claimed is:

1. A computerized method for providing patient treatment values in real-time, comprising the steps of:
   (a) providing a computer database having a plurality of predetermined categories of patient selection criteria, patient condition categories, treatment types including drug and non-drug treatment types, and precalculated treatment dosages based on the predetermined categories and patient selection criteria;
   (b) providing an input device in communication with the computer database for inputting one or more of the patient selection criteria, patient condition categories and treatment type at time of patient treatment;
   (c) providing a computer display in communication with the computer database and the input device for displaying a precalculated treatment dose based on one or more inputted patient selection criteria, patient condition categories and treatment type at time of patient treatment;
   (d) inputting, by way of the input device provided in step (b), one or more of the patient selection criteria, patient condition categories and treatment type at time of patient treatment into the computerized database provided in step (a);
   (e) determining in real-time the treatment dose, related dosage units conversion, treatment preparation, treatment administration and possible side effect information by the computer database provided in step (a), based on one or more of the patient selection criteria, patient condition categories and treatment type at time of patient treatment inputted in step (d); and
   (f) displaying the treatment dose, related dosage units conversion, treatment preparation, treatment administration and possible side effect information determined in step (e), on the computer display provided in step (c).

2. A method according to claim 1, wherein the predetermined categories of patient selection criteria comprise patient body weight ranges.

3. A method according to claim 1, wherein the predetermined categories of patient selection criteria comprise a range of selectable different colors.

4. A method according to claim 1, wherein the computerized display is configured to arrange the predetermined categories of patient selection criteria in rows and arrange the patient condition categories in columns.

5. A method according to claim 4, wherein the computerized display is configured to white out columns containing non-selected patient selection criteria.

6. A method according to claim 1, wherein the non-drug treatment types comprise equipment sizes.

7. A method according to claim 6, wherein the drug treatment types are selected from the group consisting of drug dosages and drug dosage prescribing and sequencing values.

8. A method according to claim 6, wherein the predetermined patient condition categories are selected from the group consisting of resuscitation, infusions, anaphylaxis, RSI, seizures, respiratory medicines, fluid and blood therapy, rehydration therapy, electrolyte therapy, DRA, burns and toxicology.

9. A method according to claim 1, wherein the input device includes a scanner configured to read an indicia relating to a patient selection criteria, patient condition categories, treatment types and precalculated treatment doses.

10. A method according to claim 9, wherein the scanner is a barcode scanner.

11. A method according to claim 9, wherein the indicia is a printed code affixed to treatment container.

12. A method according to claim 9, wherein the indicia is a printed code affixed to a patient chart.

13. A method according to claim 9, wherein the indicia is a printed code affixed to a patient wristband.

* * * * *